(12) United States Patent
Tajima et al.

(10) Patent No.: US 11,298,302 B2
(45) Date of Patent: Apr. 12, 2022

(54) WATER-IN-OIL TYPE EMULSION COSMETIC

(71) Applicant: SHISEIDO COMPANY, LTD., Tokyo (JP)

(72) Inventors: Shoji Tajima, Yokohama (JP); Tomoko Ikeda, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/338,145

(22) PCT Filed: Sep. 30, 2016

(86) PCT No.: PCT/JP2016/079019
§ 371 (c)(1),
(2) Date: Mar. 29, 2019

(87) PCT Pub. No.: WO2018/061181
PCT Pub. Date: Apr. 5, 2018

(65) Prior Publication Data
US 2019/0269583 A1 Sep. 5, 2019

(51) Int. Cl.
| | | |
|---|---|---|
| *A61K 8/06* | (2006.01) | |
| *A61K 8/29* | (2006.01) | |
| *A61K 8/73* | (2006.01) | |
| *A61K 8/891* | (2006.01) | |
| *A61Q 1/02* | (2006.01) | |
| *A61Q 1/12* | (2006.01) | |
| *A61K 8/896* | (2006.01) | |

(52) U.S. Cl.
CPC .............. *A61K 8/064* (2013.01); *A61K 8/29* (2013.01); *A61K 8/73* (2013.01); *A61K 8/732* (2013.01); *A61K 8/891* (2013.01); *A61K 8/896* (2013.01); *A61Q 1/02* (2013.01); *A61Q 1/12* (2013.01); *A61K 2800/43* (2013.01); *A61K 2800/612* (2013.01); *A61K 2800/651* (2013.01)

(58) Field of Classification Search
CPC ... A61Q 1/02; A61Q 1/12; A61K 8/29; A61K 8/732; A61K 8/064; A61K 8/891; A61K 2800/612; A61K 2800/651; A61K 2800/43
See application file for complete search history.

(56) References Cited

U.S. PATENT DOCUMENTS

| | | | |
|---|---|---|---|
| 6,139,829 A | 10/2000 | Estrin | |
| 2007/0134173 A1* | 6/2007 | Tanaka | A61K 8/37 424/59 |
| 2013/0243836 A1* | 9/2013 | Tanner | A61K 8/0254 424/401 |
| 2013/0323191 A1 | 12/2013 | Tanaka et al. | |
| 2013/0337026 A1* | 12/2013 | Cassin | A61K 8/0279 424/401 |
| 2015/0216787 A1* | 8/2015 | Hori | A61Q 1/04 424/59 |

FOREIGN PATENT DOCUMENTS

| | | |
|---|---|---|
| FR | 3 008 312 A1 | 1/2015 |
| JP | 2001-278743 | 10/2001 |
| JP | 2003-034627 | 2/2003 |
| JP | 2009-184980 A | 8/2009 |
| JP | 2011-256154 | 12/2011 |
| JP | 2013028567 A * | 2/2013 |
| JP | 2014-101343 A | 6/2014 |
| JP | 2014-101344 A | 6/2014 |
| JP | 2014-129261 | 7/2014 |
| JP | 2014-240382 | 12/2014 |
| JP | 2015-117236 | 6/2015 |
| WO | WO2014/128679 A1 | 8/2014 |

OTHER PUBLICATIONS

Eng. Machine Translation of Oda Yayoi (JP 2011-256154 A) cited in ISR and submitted in 1449 filed Apr. 4, 2011).*
PCT/JP2016/079019, International Search Report and Written Opinion, dated Dec. 20, 2016, 2 pages—English, 3 pages—Japanese.
PCT/JP2016/079019, Written Opinion dated Dec. 20, 2016, 5 pages—Japanese;_pages—English.
EP 16917731.8, Extended European Search Report, dated Apr. 28, 2020, 8 pages—English.
JP 2018-541832, Japanese Office Action dated Feb. 18, 2021, 6 pages—Japanese; 7 pages—English.

* cited by examiner

*Primary Examiner* — Blessing M Fubara
(74) *Attorney, Agent, or Firm* — Andrew F. Young; Nolte Lackenbach Siegel

(57) ABSTRACT

The present invention provides a water-in-oil type emulsion cosmetic which has a fresh and smooth feeling to the touch; forms a uniform coating film once applied; can make skin unevenness such as pores look less prominent while covering discolorations such as age spots and freckles; and does not give an impression of thick application. The water-in-oil emulsion cosmetic is characterized by including (A) 0.1-10% by mass of a pigment-grade titanium dioxide and (B) 0.01-2% by mass of sodium acrylate grafted starch. It is preferred that this cosmetic further includes (C) spherical particles and/or (D) a silicone elastomer.

2 Claims, No Drawings

WATER-IN-OIL TYPE EMULSION COSMETIC

CROSS REFERENCE TO RELATED APPLICATIONS

This application relates to and claims priority as a § 371 national phase, from PCT/JP2016/079019 filed Sep. 30, 2016, the entire contents of which are incorporated herein by reference.

FIGURE SELECTED FOR PUBLICATION

None

TECHNICAL FIELD

The present invention relates to a water-in-oil type emulsion cosmetic. More specifically, the present invention relates to the water-in-oil type emulsion cosmetic providing an excellent skin-correction effect with no thick-coated appearance along with providing a fresh and smooth feeling upon using.

BACKGROUND ART

Makeup cosmetics, such as a foundation, which can effectively correct (treat and mask) uneven color of the skin due to such as spots and freckles, and unevenness of the skin due to such as pores, include white pigments such as titanium dioxide and color pigments such as iron oxide. However, in some cases, a glossy finish of the makeup is lost, and the skin looks whitish and unnatural despite the skin-(irregularity)-correction effectively achieved by covering with such as titanium dioxide.

Patent Document 1 proposes a makeup cosmetic giving natural-looking finish with a transparent appearance like bare skin while covering defects of the skin by arranging powder components blended in the makeup cosmetic. In the makeup cosmetic of Patent Document 1, a composite pigment produced by coating the surface of specific plate-shaped alumina particles with iron oxide is used instead of or in addition to a conventional pigment powder. However, Patent Document 1 states that silicone-treated titanium dioxide cannot provide a transparent appearance and that the amount of the composite pigment should preferably be 10 to 35% by mass in order to obtain a sufficient covering effect, natural-looking finish, and transparent appearance with the composite pigment.

In recent years, a demand for natural-makeup giving a natural-looking finish without a thick-coated appearance has been further increasing, but as a matter of fact, a cosmetic such as a foundation must be applied repeatedly in order to sufficiently cover uneven skin-color and unevenness (concavity and convexity) of the skin, which results in the thick-coated appearance. In addition, conventional foundations in an oil gel form also have the problems of being hard to spread on the skin and being sticky.

Patent Document 2 discloses that a cosmetic comprising sodium polyacrylate starch (INCI Name) takes on a mousse form and provides a unique soft and light-feeling of use, an excellent refreshing feeling, and excellent dispersibility of a powder subjected to a specific surface treatment. However, Patent Document 2 neither discloses nor suggests the unevenness-correction effect and so on by using such a cosmetic.

CITATION LIST

Patent Documents

Patent Document 1: JP-A 2001-278743
Patent Document 2: JP-A 2011-256154

SUMMARY OF THE INVENTION

Technical Problem

In view of the background art described above, an object of the present invention is to provide a water-in-oil type emulsion cosmetic that can form a uniform (homogeneous) coated film on-and-after application and make an uneven skin due to such as pores be less noticeable by covering uneven color due to such as spots and freckles and providing a fresh and smooth feeling of use along with no thick-coated appearance.

Means to Solve the Problem

The present inventors have earnestly studied to solve the above-mentioned problems and consequently have found that a sufficient unevenness-correction effect can be obtained by blending (formulating) sodium polyacrylate starch, and that the above-effect can be obtained even if the amount of the pigment-grade titanium dioxide blended is minimized. As a result, the present invention has been completed.

That is, the present invention provides a water-in-oil emulsion cosmetic comprising:
  0.1 to 10% by mass of a pigment-grade titanium dioxide (A); and
  0.01 to 2% by mass of sodium polyacrylate starch (B).

Advantageous Effects of the Invention

The water-in-oil emulsion cosmetic of the present invention contains an appropriate amount of sodium polyacrylate starch, so that such a cosmetic can be applied to the skin lightly and mildly as if applying a mousse which provides a soft touch. The cosmetic of the present invention forms a uniform coating film to exhibit an enough skin-unevenness-correction effect even if the amount of pigment-grade titanium dioxide blended is minimized. As a result, the user is not required to apply the cosmetic overly and repeatedly, while feeling fresh and smooth in use, so that even an ordinal person, having no-special makeup skill, can attain a natural-makeup providing no thick-coated appearance.

DESCRIPTION OF EMBODIMENTS

The water-in-oil emulsion cosmetic (hereinafter, also simply referred to as "cosmetic") of the present invention comprises a pigment-grade titanium dioxide (A) and sodium polyacrylate starch (B) as indispensable (essential) components.

The applicable pigment-grade titanium dioxide (A) of the present invention is conventionally used in a variety of makeup cosmetics such as foundation. The pigment-grade titanium dioxide is considered titanium dioxide having an average particle diameter of about 200 nm to about 1 μm, and titanium dioxide of the present invention has preferably an average particle diameter of 200 nm or more.

The pigment-grade titanium dioxide (A) of the present invention preferably has a hydrophobically-treated surface. The kind of the agent for hydrophobic treatment is not particularly limited, and examples of the agent include fatty acid, higher fatty acid, higher alcohol, hydrocarbon, triglyceride, ester, silicone oil, silicone resin and fluorine compounds. Specific examples of the hydrophobically-treatment agent include alkyl modified silicone, alkyl triethoxy silane, alkyl trimethoxy silane, perfluoroalkyl phosphate, (alkyl acrylate/dimethyl silicone) copolymer, dextrin palmitate, triethoxy silylethyl polydimethylsiloxyethylhexyl dimethicone, monomethyl polysiloxane, dimethyl polysiloxane, silicone polymer and acryloyl dimethyl taurate sodium/ methacrylic amide laurate copolymer.

In Patent Document 2 mentioned above, it is necessary to treat the surface of the powder with a condensate of an acylated amino acid salt and L-lysine or L-glutamine in order to improve the dispersibility of a powder and obtain a long-lasting effect. Whereas, the present invention does not require such specific surface treatment, and hydrophobically-treated titanium dioxide, which is widely used for cosmetics, can be used.

The examples of commercially available hydrophobically-treated pigment-grade titanium dioxide applicable in the present invention include OTS-2 SACHTLEBEN RC402 (manufactured by Daito Kasei Kogyo Co., Ltd.) and SA-titanium CR-50 (manufactured by Miyoshi Kasei, Inc.).

The amount of the pigment-grade titanium dioxide (A) blended in the cosmetic of the present invention is 0.1 to 10% by mass, preferably 1 to 8% by mass, and more preferably about 2 to 5% by mass. If the amount blended is less than 0.1% by mass, a sufficient masking (concealing) effect against spots or freckles cannot be obtained, and if the amount blended is higher than 10% by mass, the spreading property becomes worth to give a powdery and unnatural finish.

The sodium polyacrylate starch (B) in the cosmetic of the present invention is a sodium salt of poly (acrylic acid) grafted on a starch and well known as a high water-absorptive polymer. Such a sodium polyacrylate starch is blended in cosmetics as an adsorbent, a binder, an emulsion stabilizer, or a hydrophilic thickener.

Although it is not particularly limited, the sodium polyacrylate starch of the present invention is a commercially available product which is available in a form of white particles. Examples of the commercially available product include Makimousse 12 (average particle diameter: about 12 μm) and Makimousse 25 (average particle diameter: about 25 μm) (both are manufactured by Daito Kasei Kogyo Co., Ltd.).

The amount of the sodium polyacrylate starch (B) blended in the cosmetic of the present invention is 0.01 to 2% by mass, preferably 0.05 to 1% by mass, and more preferably 0.1 to 0.5% by mass. If the blended amount is less than 0.01% by mass, a fresh and smooth feeling of use cannot be obtained, and the skin-unevenness-correction effect becomes insufficient. If the blended amount is higher than 2% by mass, the cosmetic film tends to be "creased".

The cosmetic of the present invention preferably contains, in addition to the indispensable components (A) and (B), a spherical powder (C) and/or a silicone elastomer (D).

In addition, the spherical powder (C) further improve the feeling of use and effectively the skin-unevenness-correction.

The spherical powder (C) used in the present invention can be a substantially spherical powder, which includes right-spherical powder and oblate shape powder, that is generally used in cosmetics.

Preferred examples of the spherical powder include a spherical silicone powder; a spherical silica powder; and a spherical organic resin powder such as nylon, urethane, polymethyl methacrylate, polyethylene, or polypropylene. According to the present invention, the spherical particles particularly capable of absorbing a high-amount of oils are preferable for use and a spherical nylon powder is further preferable therefor.

A commercially available spherical powder can be used. Examples of the commercially available spherical silicone powder include KSP-300 (manufactured by Shin-Etsu Chemical Co., Ltd.); Trefil E-506S, Trefil E-508, 9701 Cosmetic Powder, EP-9215 Cosmetic Powder, EP-9261 TI Cosmetic Powder, and EP-9293 AL Cosmetic Powder (all manufactured by Dow Corning Toray Co., Ltd.), which are spherical (dimethicone/vinyl dimethicone) crosspolymer powders; and TOSPEARL® 120A, TOSPEARL® 145A, and TOSPEARL® 2000B (all manufactured by Momentive Performance Materials Inc.), which are spherical polymethylsilsesquioxane powders.

Examples of the commercially available spherical silica powder include Silica Microbead P-1500 (manufactured by JGC Catalysts and Chemicals Ltd.) and SUNSPHERE® L-51 (manufactured by AGC Inc.).

Examples of the commercially available spherical organic resin powder include spherical PMMA powder particles (Ganzpearl® GMX-0810: manufactured by Ganz Chemical Co., Ltd., and Matsumoto Microsphere® series M-100 and M-330: manufactured by Matsumoto Yushi-Seiyaku Co., Ltd.) and spherical urethane particles (Plastic Powder D-400: manufactured by Toshiki Pigment Co., Ltd.).

The amount of the spherical powder (C) blended in the cosmetic of the present invention is 0.1 to 30% by mass, preferably 2 to 10% by mass, and more preferably 3 to 8% by mass. If the blended amount is less than 0.1% by mass, the effects of the blended spherical powder cannot be provided, and if the blended amount is higher than 30% by mass, the freshness feeling is rather lost.

The suppression of rough-powdery property and the improvement as for freshness become further remarkably excellent by blending the silicone elastomer (D) in the cosmetic of the present invention.

The silicone elastomer (D) of the present invention is either a crosslinked or non-crosslinked silicone resin powder (elastomer). In particular, a polyether-modified silicone elastomer capable of emulsifying is preferred.

Examples of a crosslinked and incapable of emulsifying silicone elastomer of the present invention include one or at least two crosslinked silicone resin powders, such as (dimethicone/phenylvinyl dimethicone) crosspolymer, (dimethicone/vinyl dimethicone/methicone) crosspolymer, (dimethicone/vinyl dimethicone) crosspolymer, dimethicone crosspolymer, and (diphenyl dimethicone/vinyl diphenyl dimethicone/silsesquioxane) crosspolymer.

A silicone elastomer capable of emulsifying (also referred to as a silicone surfactant), which is preferably used, is a polyether-modified silicone having a polyoxyalkylene structure introduced into the silicone skeleton thereof. For example, a crosslinked product obtained by crosslinking a silicone chain with a polyoxyalkylene chain and a branched chain polyether-modified silicone obtained by introducing a polyoxyalkylene group into the side of the silicone chain are preferably used.

Specific examples of the silicone elastomer capable of emulsifying include polyether-modified silicones, such as PEG-10 dimethicone, PEG-9 polydimethylsiloxyethyl dimethicone, lauryl PEG-9 polydimethylsiloxyethyl dimethicone, and lauryl PEG-15 polydimethylsiloxyethyl dimethicone; and crosslinked polyether-modified silicones, such as (dimethicone/(PEG-10/15)) crosspolymer and (dimethicone/polyglycerol-3) crosspolymer, and one or at least two of such silicon elastomers can be mixed and blended in cosmetics.

The silicone elastomer of the present invention can be blended as a silicone gel consisting of an elastomer and a solvent, regardless of capability of emulsifying. Such silicone gel is commercially available product, and examples thereof include KSG-18A, KSG-16, and KSG-15AP (all manufactured by Shin-Etsu Chemical Co., Ltd.), Elastomer Blend DC9045 (manufactured by Dow Corning Toray Co., Ltd.), and KSG-210, KSG-710, and KSG-360Z (all manufactured by Shin-Etsu Chemical Co., Ltd.).

The amount of the silicone elastomer (D) blended in the cosmetic of the present invention is 0.1 to 30% by mass, preferably 2 to 10% by mass, and more preferably 3 to 8% by mass. If the amount blended is less than 0.1% by mass, the effects of the blended silicone elastomer is attainable, and if the amount blended is higher than 30% by mass, the freshness is rather lost.

The cosmetic of the present invention is a water-in-oil type emulsion cosmetic composition. The oil, constituting the cosmetic of the present invention, is not particularly limited and can be appropriately selected from a group consisting of hydrocarbon oils, ester oils, waxes, and silicone oils. It is particularly preferred to blend a silicone oil, especially a volatile cyclic or linear silicone oil, from the viewpoint of the feeling of use.

Although the amount of water blended in the water-in-oil emulsion cosmetic of the present invention is not particularly limited and, for example, the cosmetic can be prepared with about 30% by mass or less, about 25% by mass or less or about 20% by mass of water.

The cosmetic of the present invention can contain another optional component that can be blended into a water-in-oil emulsion cosmetic composition within a range that does not impair the effects of the scope of the present invention. Examples of another optional component include, but not limited to, other powder components (excluding the pigment-grade titanium dioxide (A) and the spherical powder (C)), alcohols, polyols, dyes, pH adjusters, moisturizers, thickeners (excluding the sodium polyacrylate-starch (B)), surfactants, dispersants, stabilizers, colorants, preservatives, antioxidants, UV absorbers and fragrances.

Examples of the other powder components include color pigments, such as titanium dioxide microparticles, zinc oxide microparticles, red iron oxide, yellow iron oxide, black iron oxide, ultramarine blue, cerium oxide, talc, mica, sericite, kaolin, bentonite, clay, silicic acid, silicic anhydride, magnesium silicate, zinc stearate, fluorine-containing phlogopite, synthetic talc, barium sulfate, magnesium sulfate, calcium sulfate, boron nitride, bismuth oxychloride, alumina, zirconium oxide, magnesium oxide, chromium oxide, calamine, magnesium carbonate, and complexes thereof; inorganic pigments; inorganic powders containing extenders; and organic resin powders other than the above spherical powders. Such powder components can be surface-treated.

The cosmetic of the present invention can be produced according to a conventional method for water-in-oil emulsion cosmetics. That is, the cosmetic can be produced by stirring to emulsify an aqueous phase in a separately prepared oil phase under heating, if necessary.

The cosmetic of the present invention is particularly suitable for a makeup cosmetic such as a foundation. Accordingly, it is preferable to provide the cosmetic of the present invention in the form of, for example, a liquid foundation, a makeup base, a BB ("blemish balm") cream or a CC ("color control") cream.

EXAMPLES

The present invention will now be described in further detail with reference to Examples, but the present invention is not limited to these Examples at all. The amount of each component is indicated in % by mass based on the total amount of the composition in which the component is blended, unless otherwise specified.

A water-in-oil emulsion foundations having the formula shown in Tables 1 and 2 were prepared according to a conventional method. The foundation prepared for each example was evaluated as for the following terms by expert panel members.

Evaluation Terms:
(1) Freshness at the application
(2) Smoothness (lightness) at the application
(3) Uniformity of the coated film
(4) No thick-coated impression
(5) Capability of covering the uneven color (spots and freckles)
(6) Correction effect on unevenness (concavity and convexity) (e.g., pores)

Evaluation Results:
A++: Extremely excellent
A+: Excellent
B: Good
C: Poor
D: Very poor

TABLE 1

|  | Example 1 | Example 2 | Example 3 | Comparative Example 1 | Comparative Example 2 |
| --- | --- | --- | --- | --- | --- |
| Decamethylcyclopentasiloxane | 23.41 | 23.16 | 22.66 | 23.66 | 18.06 |
| Dimethicone | 9 | 9 | 9 | 9 | 9 |
| Diethylhexyl succinate | 1 | 1 | 1 | 1 | 1 |
| Octyl methoxycinnamate | 2 | 2 | 2 | 2 | 2 |
| PEG-10 dimethicone | 2.5 | 2.5 | 2.5 | 2.5 | 2.5 |
| Polyglyceryl-2 diisostearate | 1 | 1 | 1 | 1 | 1 |
| (PEG-15/lauryl polydimethylsiloxyethyl dimethicone) crosspolymer | 1 | 1 | 1 | 1 | 1 |
| Sodium polyacrylate starch (1) | 0.25 | 0.5 | 1 | — | 1 |
| Stearic acid-treated titanium dioxide | 8 | 8 | 8 | 8 | 8 |
| Pigment grade titanium dioxide (2) | 2.4 | 2.4 | 2.4 | 2.4 | 12 |
| Barium sulfate | 3 | 3 | 3 | 3 | 3 |
| Silicone-treated iron oxide (red) | 0.279 | 0.279 | 0.279 | 0.279 | 0.279 |

TABLE 1-continued

|  | Example 1 | Example 2 | Example 3 | Comparative Example 1 | Comparative Example 2 |
|---|---|---|---|---|---|
| Silicone-treated iron oxide (yellow) | 0.864 | 0.864 | 0.864 | 0.864 | 0.864 |
| Silicone-treated iron oxide (black) | 0.045 | 0.045 | 0.045 | 0.045 | 0.045 |
| Spherical nylon powder | 8 | 8 | 8 | 8 | 8 |
| Ion-exchanged water | 27.752 | 27.752 | 27.752 | 27.752 | 22.752 |
| EDTA-2Na2H$_2$O | 0.2 | 0.2 | 0.2 | 0.2 | 0.2 |
| Erythritol | 1 | 1 | 1 | 1 | 1 |
| Xylitol | 1 | 1 | 1 | 1 | 1 |
| Citric acid | 0.02 | 0.02 | 0.02 | 0.02 | 0.02 |
| Sodium citrate | 0.08 | 0.08 | 0.08 | 0.08 | 0.08 |
| Sodium dehydroacetate | 0.2 | 0.2 | 0.2 | 0.2 | 0.2 |
| Dynamite glycerol | 3 | 3 | 3 | 3 | 3 |
| Ethanol | 3.5 | 3.5 | 3.5 | 3.5 | 3.5 |
| Phenoxyethanol | 0.5 | 0.5 | 0.5 | 0.5 | 0.5 |
| Total | 100 | 100 | 100 | 100 | 100 |
| Freshness | A+ | A+ | A+ | A+ | C |
| Smoothness | A+ | A+ | A+ | A | C |
| Uniformity of the coated film | A+ | A | B | A+ | B |
| No thick-coated impression | A+ | A+ | A+ | A+ | D |
| Capability of covering the uneven color | A | A | A | A | A+ |
| Correction effect on unevenness | A+ | A+ | A+ | C | A |

(1) MAKIMOUSSE 25 (manufactured by Daito Kasei Kogyo Co., Ltd.)
(2) OTS-RC402P (manufactured by Daito Kasei Kogyo Co., Ltd.)

It is obvious from the results shown in Table 1 that the evaluation results for Examples 1 and 2, including 2.4% by mass of pigment-grade titanium dioxide and 0.5% by mass or less of sodium polyacrylate starch, are all excellent with regard to evaluation terms. With regard to Example 3, including the more amount of sodium polyacrylate starch by 1% by mass, the uniformity of coated film slightly is inferior regardless still at the good level, which is considered not problematic for a product, and other evaluation terms are excellent overall. Whereas, with regard to Comparative Example 1, not including sodium polyacrylate starch, the unevenness-correction effect is poor, and with regard to Comparative Example 2, including the pigment-grade titanium dioxide more than 10% by mass, capability of covering the uneven color and the unevenness-correction effect are attained, but the freshness and smoothness are poor and not-acceptable due to occurrences of the rough-powdery property and the thick-coated impression.

TABLE 2

|  | Example 4 | Example 5 | Example 6 | Example 7 | Example 8 | Example 9 |
|---|---|---|---|---|---|---|
| Decamethylcyclopentasiloxane | 37.415 | 37.415 | 37.415 | 37.415 | 37.415 | 37.415 |
| Dimethicone | 8 | 8 | 8 | 8 | 8 | 8 |
| PEG-10 dimethicone | 2.5 | 2.5 | 2.5 | 2.5 | 2.5 | 2.5 |
| Polyglyceryl-2 diisostearate | 1 | 1 | 1 | 1 | 1 | 1 |
| Tocopherol | 0.02 | 0.02 | 0.02 | 0.02 | 0.02 | 0.02 |
| (Dimethicone/polyglycerin-3) crosspolymer | 1 | 1 | 1 | 1 | 1 | 1 |
| Sodium polyacrylate starch (1) | 0.25 | 0.25 | 0.25 | 0.25 | 0.25 | 0.25 |
| Stearic acid-treated titanium dioxide | 11 | 11 | 11 | 11 | 11 | 11 |
| Pigment grade titanium dioxide (2) | 6 | 6 | 6 | 6 | 6 | 6 |
| Silicone-treated iron oxide (red) | 0.35 | 0.35 | 0.35 | 0.35 | 0.35 | 0.35 |
| Silicone-treated iron oxide (yellow) | 1.24 | 1.24 | 1.24 | 1.24 | 1.24 | 1.24 |
| Silicone-treated iron oxide (black) | 0.025 | 0.025 | 0.025 | 0.025 | 0.025 | 0.025 |
| Spherical nylon powder | 5 | — | — | — | — | — |
| Spherical cellulose powder | — | 5 | — | — | — | — |
| Spherical PMMA powder | — | — | 5 | — | — | — |
| Spherical silicone resin powder | — | — | — | 5 | — | — |
| Spherical nonporous silica powder | — | — | — | — | 5 | — |
| Spherical silica powder | — | — | — | — | — | 5 |
| Ion-exchanged water | 18 | 18 | 18 | 18 | 18 | 18 |
| EDTA-2Na2H2O | 0.2 | 0.2 | 0.2 | 0.2 | 0.2 | 0.2 |
| Glycerol | 4 | 4 | 4 | 4 | 4 | 4 |
| Ethanol | 3.5 | 3.5 | 3.5 | 3.5 | 3.5 | 3.5 |
| Phenoxyethanol | 0.5 | 0.5 | 0.5 | 0.5 | 0.5 | 0.5 |
| Total | 100 | 100 | 100 | 100 | 100 | 100 |
| Smoothness | A+ | A+ | A | A+ | A | A |
| Freshness | A+ | A | A | A | A | A |

TABLE 2-continued

|  | Example 4 | Example 5 | Example 6 | Example 7 | Example 8 | Example 9 |
|---|---|---|---|---|---|---|
| Uniformity of applicate | A+ | A+ | A | A+ | A+ | A+ |
| Capability of covering the uneven color | A | A | A | A | A | A |
| Correction effect on the unevenness | A+ | A+ | A+ | A+ | A+ | A+ |

(1) MAKIMOUSSE25 (manufactured by Daito Kasei Kogyo Co., Ltd.)
(2) OTS-RC402P (manufactured by Daito Kasei Kogyo Co., Ltd.)

As shown in Table 2, the evaluation results with regard to all terms are above Excellent and well acceptable despite the type variation of the spherical powder.

TABLE 3

|  | Example 10 | Example 11 | Example 12 |
|---|---|---|---|
| Decamethylcyclopentasiloxane | 42.415 | 38.415 | 43.315 |
| Dimethicone | 8 | 8 | 8 |
| PEG-10 dimethicone | 2.5 | 2.5 | 2.5 |
| Polyglyceryl-2 diisostearate | 1 | 1 | 1 |
| Tocopherol | 0.02 | 0.02 | 0.02 |
| (Dimethicone/polyglycerin-3) crosspolymer | 1 | — | 1 |
| Sodium polyacrylate starch (1) | 0.25 | 0.25 | 0.25 |
| Stearic acid-treated titanium dioxide | 11 | 11 | 11 |
| Pigment grade titanium dioxide (2) | 6 | 6 | 0.1 |
| Silicone-treated iron oxide (red) | 0.35 | 0.35 | 0.35 |
| Silicone-treated iron oxide (yellow) | 1.24 | 1.24 | 1.24 |
| Silicone-treated iron oxide (black) | 0.025 | 0.025 | 0.025 |
| Spherical nylon powder | — | 5 | 5 |
| Ion-exchanged water | 18 | 18 | 18 |
| EDTA-2Na2H2O | 0.2 | 0.2 | 0.2 |
| Glycerol | 4 | 4 | 4 |
| Ethanol | 3.5 | 3.5 | 3.5 |
| Phenoxyethanol | 0.5 | 0.5 | 0.5 |
| Total | 100 | 100 | 100 |
| Smoothness | A | A+ | A+ |
| Freshness | A+ | A+ | A+ |
| Uniformity of applicate | A+ | A+ | A+ |
| Capability of covering the uneven color | A | A | B |
| Correction effect on unevenness | B | B | B |

(1) MAKIMOUSSE 25 (manufactured by Daito Kasei Kogyo Co., Ltd.)
(2) OTS-RC402P (manufactured by Daito Kasei Kogyo Co., Ltd.)

As shown in Table 3, Examples 10 and 11, not including either spherical powder or elastomer, are slightly ineffective on the unevenness correction, but are still at a good level at which no problem takes place for a product. In addition, in Example 12, including a lesser amount, 0.1% by mass, of pigment-grade titanium dioxide, capability of covering the uneven color and correction effect on the unevenness slightly decrease, but such levels are considered not problematic for a product.

Another formulation of the water-in-oil emulsion cosmetic according to the present invention is shown below. The evaluation results, with regard to the cosmetic prepared according to such a formulation, are the same as the results with regard to Example 1.

Formulation Example 1: Water-in-Oil Emulsion Foundation

| Component | Amount blended (% by mass) |
|---|---|
| (1) Dimethylpolysiloxane | 36.88 |
| (2) Decamethylcyclopentasiloxane | 10.00 |
| (3) Methylpolysiloxane | 3.00 |
| (4) PEG-10 dimethicone | 3.00 |
| (5) Polyglyceryl-2 diisostearate | 1.00 |
| (6) Fragrance | 0.10 |
| (7) (Dimethicone/polyglycerol-3) crosspolymer | 1.00 |
| (8) Isononyl isononanoate | 3.00 |
| (9) Disteardimonium hectorite | 1.00 |
| (10) Nylon-12 | 5.00 |
| (11) Hydrophobized titanium dioxide microparticles | 5.00 |
| (12) Hydrophobic-treated pigment grade titanium dioxide | 3.00 |
| (13) Hydrophobic-treated yellow iron oxide | 1.25 |
| (14) Hydrophobic-treated red iron oxide | 0.35 |
| (15) Hydrophobic-treated black iron oxide | 0.02 |
| (16) Sodium polyacrylate starch | 0.30 |
| (17) Ion-exchanged water | 18.00 |
| (18) 1,3-Butylene glycol | 5.00 |
| (19) Glycerol | 3.00 |
| (20) Preservative | 0.10 |

Production method comprises steps of:
(i) adding powders (10) to (16) to a mixture of oil phase components (1) to (9), followed by stirring and mixing the mixture with such as homomixer to obtain a powder dispersion (oil phase).
(ii) adding an aqueous phase of the components (17) to (20), which are mixed in advance and standing, to the powder dispersion (oil phase), followed by stirring and mixing the mixture with such as homomixer into an emulsion to obtain an emulsified foundation.

The invention claimed is:
1. A water-in-oil emulsion cosmetic, comprising:
(A) 2 to 8% by mass of a pigment-grade titanium dioxide having an average particle diameter of 200 nm to 1 µm;
(B) 0.01 to 2% by mass of a sodium polyacrylate starch;
(C) 2 to 10% by mass of a spherical powder; and
(D) 1 to 10% by mass of a silicone elastomer;
wherein said (D) silicone elastomer comprises at least one silicone elastomer capable of emulsifying the composition and selected from the group consisting of PEG-10 dimethicone, PEG-9 polydimethylsiloxyethyl dimethicone, lauryl PEG-9 polydimethylsiloxyethyl dimethicone, and lauryl PEG-15 polydimethylsiloxyethyl dimethicone, (dimethicone/(PEG-10/15)) crosspolymer and (dimethicone/polyglycerol-3) crosspolymer.
2. The water-in-oil emulsion cosmetic according to claim 1, wherein: said spherical powder (C) is at least one selected from the group consisting of a spherical silicone powder, a spherical silica powder, a nylon spherical powder, a urethane spherical powder, a polymethyl methacrylate spherical powder, a polyethylene spherical powder, and a polypropylene spherical powder.

\* \* \* \* \*